United States Patent
Albrektsson et al.

(10) Patent No.: US 6,824,568 B1
(45) Date of Patent: Nov. 30, 2004

(54) IMPLANT

(75) Inventors: Tomas Albrektsson, Göteborg (SE); Lars Carlsson, Kullavik (SE); Magnus Jacobsson, Göteborg (SE); Warren Macdonald, Bournemouth (GB); Stig Wennberg, Gunnilse (SE)

(73) Assignee: Astra Tech AB, Molndal (SE)

( * ) Notice: Subject to any disclaimer, the term of this patent is extended or adjusted under 35 U.S.C. 154(b) by 0 days.

(21) Appl. No.: 10/089,864
(22) PCT Filed: Oct. 6, 2000
(86) PCT No.: PCT/SE00/01944
§ 371 (c)(1),
(2), (4) Date: Jun. 25, 2002
(87) PCT Pub. No.: WO01/24737
PCT Pub. Date: Apr. 12, 2001

(30) Foreign Application Priority Data

Oct. 6, 1999 (SE) ............................................... 9903607
Oct. 6, 1999 (SE) ............................................... 9903612

(51) Int. Cl.⁷ .................................................. A61F 2/36
(52) U.S. Cl. .................................. 623/23.15; 623/23.27
(58) Field of Search ........................... 623/23.14, 23.12, 623/23.15, 23.18, 23.21, 23.24, 23.25, 23.26, 23.27, 23.35, 23.44

(56) References Cited

U.S. PATENT DOCUMENTS

| 3,051,169 | A | * | 8/1962 | Grath | 128/92 |
| 3,996,625 | A | | 12/1976 | Noiles | |
| 4,059,102 | A | * | 11/1977 | Devas | 128/92 B |
| 4,978,350 | A | | 12/1990 | Wagenknecht | |
| 5,259,398 | A | * | 11/1993 | Vrespa | 128/898 |

FOREIGN PATENT DOCUMENTS

| EP | 0 368 488 A1 | | 5/1990 | | |
| EP | 0 441 557 A2 | | 8/1991 | | |
| FR | A059919 | * | 9/1954 | | 623/23 |
| WO | 93/16663 | * | 9/1993 | | 623/23 |

* cited by examiner

Primary Examiner—Bruce E Snow
(74) Attorney, Agent, or Firm—Birch, Stewart, Kolasch & Birch, LLP

(57) ABSTRACT

An implant (1) for insertion into and permanent anchorage in bone tissue having an intraosseous anchoring structure (3). The anchoring structure (3) has a generally circular cross-section and comprises a first cylindrical section (11) of a first diameter, a second cylindrical section (13) of a second diameter less than the first diameter, said first and second cylindrical sections (11, 13) each being provided with a screw thread profile. The anchoring structure (3) also comprises a tapered connecting section (15) provided between an interconnecting said first and second cylindrical sections (11, 13).

34 Claims, 9 Drawing Sheets

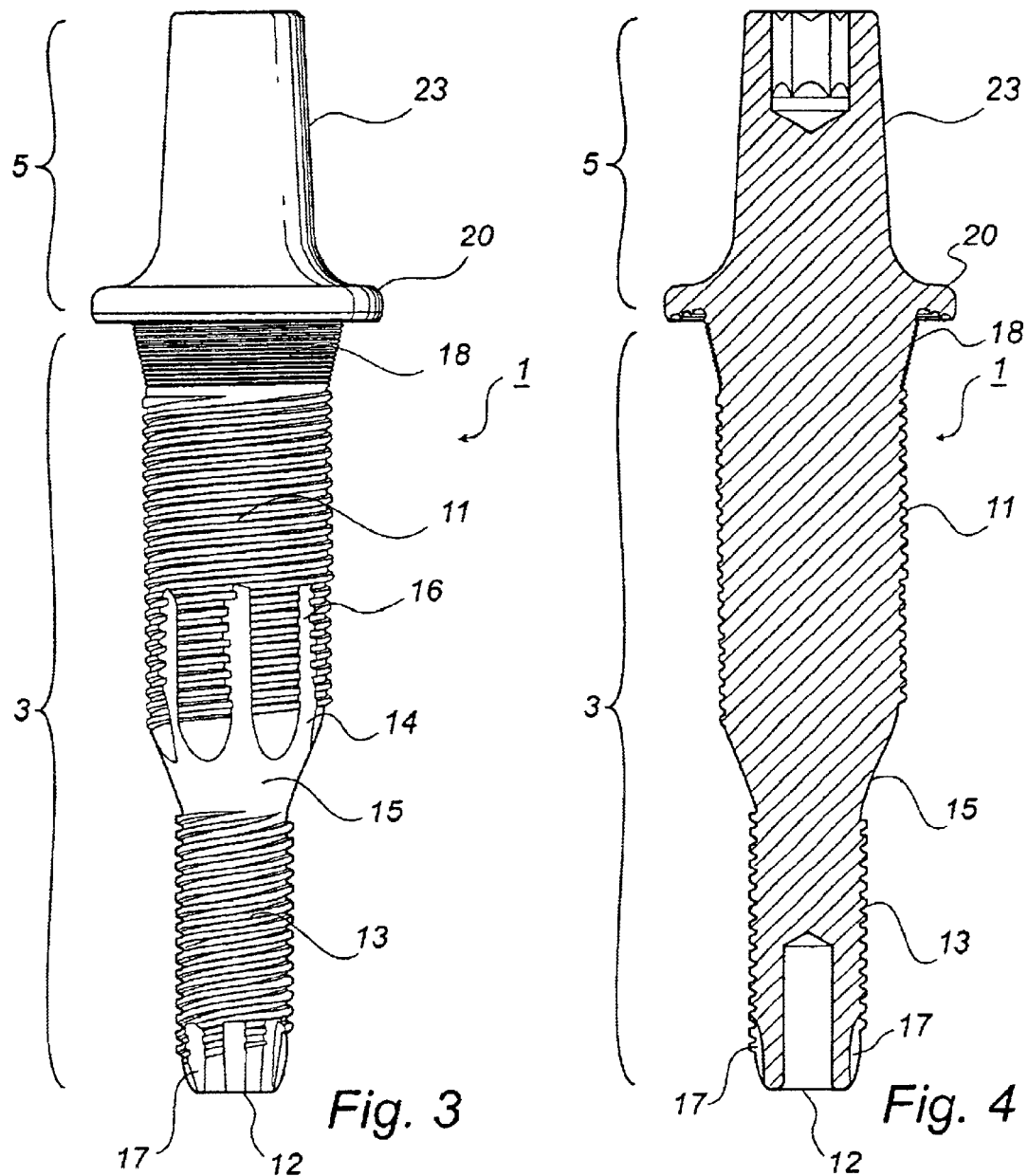

IMPLANT

This application is the national phase under 35 U.S.C. §371 of PCT International Application No. PCT/SE00/01944 which has an International filing date of Oct. 6, 2000, which designated the United States of America.

FIELD OF THE INVENTION

The present invention relates to an implant for insertion into and permanent anchorage in human skeletal or bone tissue. More specifically, the invention concerns an implant having a screw-threaded anchoring structure comprising a first cylindrical section of a first diameter and a second cylindrical section of a second diameter, said second diameter being less than said first diameter.

The invention is particularly, although not exclusively, concerned with an implant of this type which takes the form of a femur fixture for a hip-joint pros* thesis.

BACKGROUND OF THE INVENTION

Implants of this type in the form of femur fixtures for a hip-joint prosthesis are known from Applicant's prior International patent application publications WO93/01769, WO93/16663 and WO97/25939 with the first and second cylindrical sections being provided with external screw threads for engaging the bone tissue of the femur. The screw threaded first and second cylindrical sections of the femur fixture-disclosed in WO93/01769 are assembled together in the femur by firstly inserting the second cylindrical section medially into the neck of the femur from beneath the greater trochanter and then inserting the first cylindrical section into the neck laterally through the resected section left after resection of the head of the femur. The screw threaded first and second cylindrical sections of the femur fixture disclosed in WO93/16663 and WO97/25939, on the other hand, are integrally formed or pre-assembled prior to anchorage of the fixture in the femur neck by screwing the fixture into the femur neck laterally through the resected section left after resection of the femur head.

In the femur fixtures disclosed in WO93/01769, WO93/16663 and WO97/25939, the first cylindrical section steps into the second cylindrical section. A drawback of this type of implant is the amount of stress present between the bone and the implant following implantation.

SUMMARY OF THE INVENTION

Thus, the object of the present invention is to provide an implant where the above mentioned drawback is reduced.

This and other objects are achieved according to the present invention by providing an implant having the features defined in the independent claim. Preferred embodiments are defined in the dependent claims.

According to the present invention there is provided an implant for insertion into and permanent anchorage in bone tissue, comprising an intraosseous anchoring structure of a generally circular cross-section, said anchoring structure comprising a first cylindrical section of a first diameter and a second cylindrical section of a second diameter, said second diameter being less than said first diameter, said first and second cylindrical sections each being provided with a screw thread profile. The implant is characterised in that said anchoring structure comprises a tapered connecting section provided between and interconnecting said first and second cylindrical sections.

The implant of the invention may be an orthopaedic implant, for example a femur fixture for a hip-joint prosthesis as in the embodiment hereinafter to be described.

Thus, the present invention is based on the advantageous idea of providing an implant of the above-mentioned type with a tapered connecting section between the first and second screw-threaded, cylindrical sections.

The provision of a tapered connecting section would overcome the drawback mentioned above and provide a number of additional advantages. First, the stresses induced by the sharp, step-wise transition present in the prior art implants between the cylindrical sections of differing diameters is radically reduced using the tapered connecting section of the present invention.

A further advantage resulting from the provision of a tapered connecting section when the implant is used for implantation in a cavity of corresponding shape formed in bone tissue, is that the insertion of the implant is facilitated. This is because the distal end of the implant can be guided by the tapered section of the cavity which is arranged for interacting with the tapered connecting section. Thus, the cavity will have no surface facing directly opposite the insertion direction of the implant, as is the case with the prior art implants (see item 50 of FIG. 5 in WO 97/25939).

A still further advantage is that the provision of a tapered connecting section provides a wedging effect during implantation of the implant into bone tissue. This wedging effect improves the short and long term stability of the implant following said implantation. This is mainly due to the radial force component of the normal contact force between the implant and the cancellous bone tissue that surrounds the connecting section upon implantation.

If the longitudinal force exerted by the surrounding tissue on the implant of the invention and on the above-mentioned prior art implants, following implantation of the implant, is essentially the same, then the transversal force on the implant of the invention will be greater compared to the prior art stepped implants. This is because the longitudinal force is carried by the inclined surface of the tapered connecting section, whereby the resulting transversal force will have a radial force component. This radial force component is not present in the prior art implants since only the radial end portion (e.g. item 10 of FIG. 1 in WO 97/25939) of the proximal cylindrical section (e.g. item 2 of FIG. 1 in WO 97/25939) carries the corresponding longitudinal force.

While the overall transversal force is increased, the actual force per surface unit is not necessarily increased. This is due to the fact that the contact surface carrying the longitudinal contact forces will be considerably greater with the tapered connecting section of the present invention as is the case with said radial end portion of the prior art implants.

Also, the provision of the inventive tapered connecting section improves the integration between the implant and the cancellous bone tissue (termed "osseointegration" in the art). This is mainly due to the shape of the contact surface of the connecting section, but also to the increased overall contact force exerted on the implant by the cancellous bone tissue.

Ordinarily, the first cylindrical section is disposed proximally of the second cylindrical section with the taper of the connecting section inclining inwardly in the distal direction, as in the embodiment hereinafter to be described.

Preferably, the tapered connecting section has a frustoconical profile, even though other tapering shapes are conceivable without departing from the scope of the present invention.

According to preferred embodiments of the invention, the diameter of the first cylindrical section is adapted to the actual size and shape of the femur of the particular patient for whom the implant is intended. Thus, the diameter of the first cylindrical section can vary considerably. However, the diameter of the second cylindrical portion is preferably dimensioned to be within a short, limited range. Thus, the flank angle of the connecting section may vary in dependence of the actual dimensions of the first and second cylindrical sections. Preferably, the flank angle can be varied in the range of 10°–50°, and more preferably in the range of 200–400.

Furthermore, the longitudinal extension of the connecting section is preferably in the range of 5–15 mm, preferably in the range of 7–11 mm.

Advantageously, the end of the tapered connecting section interfacing the first cylindrical section has essentially the same diameter as the first cylindrical section. Likewise, the end of the tapered connecting section interfacing the second cylindrical section advantageously has essentially the same diameter as the second cylindrical section.

According to preferred embodiments of the invention, the connecting section is at least partly provided with a roughened surface. This would even further promote the osseointegration process at the transition area between the cylindrical sections. The roughened surface could be achieved through blasting, preferably grit-blasting, etching, or the like. Alternatively or additionally, a circumferentially oriented roughness, preferably machined, could be provided on the connecting section. Such circumferentially oriented roughness could for instance be provided in the form of grooves, beads, tracks, or screw threads.

According to preferred embodiments of the invention the tapered connecting section is at least partly provided with a screw thread profile. The screw thread profile of the tapered connecting section is preferably different from the screw thread profiles on the first and second cylindrical sections. Preferably, the height of the screw thread profile of the connecting section is less than the height of the screw thread profiles of the cylindrical sections. Advantageously, the screw thread profile of the connecting section are in the form of microthreads having a height of less than 0.3 mm, preferably in the range of 0.1–0.25 mm, even more preferably about 0.2 mm.

Other differences in screw thread profiles are also conceivable, such as the screw thread profile of the connecting section having a pitch less than the pitch of the screw thread profiles of the cylindrical sections.

Alternatively, the screw thread profile of the connecting section is essentially the same as that of the cylindrical sections.

Where the circumferential roughness is provided in the form of beads or tracks, the height of said circumferential roughness is preferably less than 0.3 mm, more preferably in the range of 0.1–0.25 mm, and even more preferably approximately 0.2 mm.

Alternatively, at least part of the surface or the entire surface of the connecting section may be left smooth, or even polished.

In an embodiment of the invention, such as the one hereinafter to be described, one or more self-tapping cutting recesses are provided at least in part on the tapered connecting section. Said cutting recesses preferably being equispaced and circumferentially arranged.

According to preferred embodiments of the invention, the implant also comprises a tapered proximal section interconnecting the first cylindrical portion with a head section of the implant. The tapered proximal section provides increased contact between the implant and surrounding cortical bone tissue and improves the stability of the implant when anchored in bone tissue.

The tapered proximal section advantageously has a frustoconical shape with a flank angle that is preferably in the range of 8°–150, and even more preferably in the range of 100–130, and even more preferably approximately 12°. Preferably, the end of the tapered proximal section abutting the first cylindrical section has a diameter essentially equal to the diameter of the first cylindrical section.

Preferably, the surface of the tapered proximal section is provided with a circumferentially oriented roughness, for instance in the form of circumferential beads or screw threads. The height of the beads or screw threads is preferably no greater than 0.3 mm, more preferably in the range of 0.1–0.25 mm, and even more preferably approximately 0.2 mm.

Preferably, said beads or screw threads engage with the cortex 34 of the femur neck at the resected surface. As a result, a stronger short term anchorage of the implant is provided. Also, a stronger long term anchorage is provided due to the improved osseointegration between the tapered proximal section and the surrounding bone tissue.

According to embodiments of the present invention, the above-mentioned head section is provided with a collar abutting the tapered proximal section, which collar delimits the insertion of the implant into bone tissue. Preferably, the surface of the collar facing the proximal section is inclined inwardly so as to mate with a resected bone tissue surface that has been given a correspondingly inclined shape. Preferably, the angle of inclination is within the range of 100–200, preferably approximately 15°. Alternatively, the surface of the collar facing the proximal section is given a concave shape, so as to mate with a convex bone tissue surface. Thereby, an improved contact between the implant and the bone surface can be obtained.

Preferably, said collar surface is provided with radially spaced circular beads or grooves for increasing the stability of the inserted implant and promote the osseointegration between the implant and the bone tissue. Preferably, these beads have a height in the range of 0.1–0.5 mm, preferably in the range of 0.2–0.4 mm, and even more preferably approximately 0.3 mm.

By way of example, an embodiment of the invention will now be described with reference to the accompanying Figures of drawings.

BRIEF DESCRIPTION OF THE DRAWINGS

FIG. 3 is a longitudinal side view of the femur fixture, FIG. 4 is a longitudinal sectional view of the femur fixture.

DESCRIPTION OF EXEMPLARY EMBODIMENT

Figure 1:
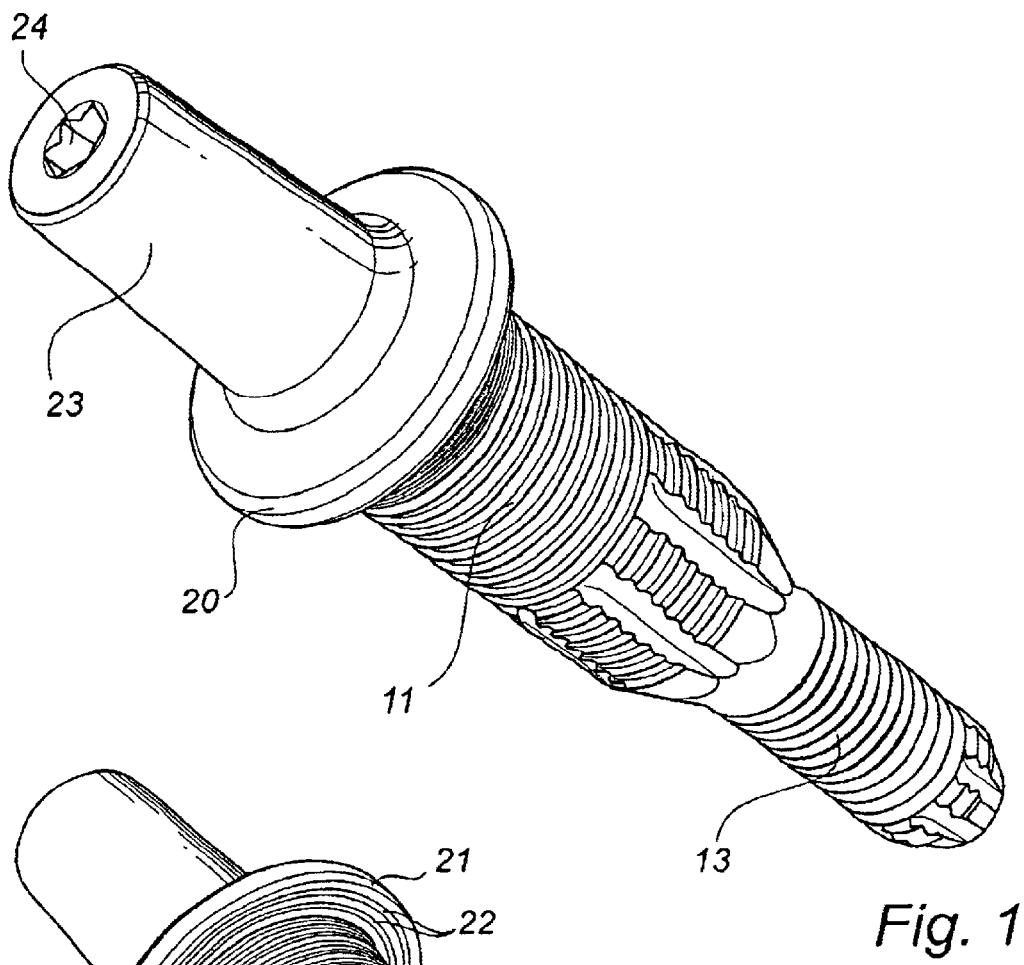
FIG. 1 is a perspective view of a femur fixture for a hip-joint prosthesis in accordance with an embodiment of the invention.

With reference to FIGS. 1–8, there is shown an integrally formed femur fixture 1 for a hip-joint prosthesis preferably made from commercially pure titanium and consisting of (i) an intraosseous anchoring section 3 of circular cross-section, and (ii) a head section S. The anchoring section 3 is intended for insertion laterally into a cavity 30 of complementary profile (FIG. 7), said cavity 30 being drilled into the neck of a femur through a resected section 33 made by resection of the head of the femur. The head section 5 of the fixture, which will protrude from the resected section 33 when the intraosseous anchoring section 3 is located in the cavity 30 (FIG. 8), is arranged for supporting a ball 25 of the hip-joint prosthesis which interacts with the anatomical acetabular cavity or an acetabular part of the hip-joint prosthesis where a total hip-joint prosthesis is required.

Figure 2:
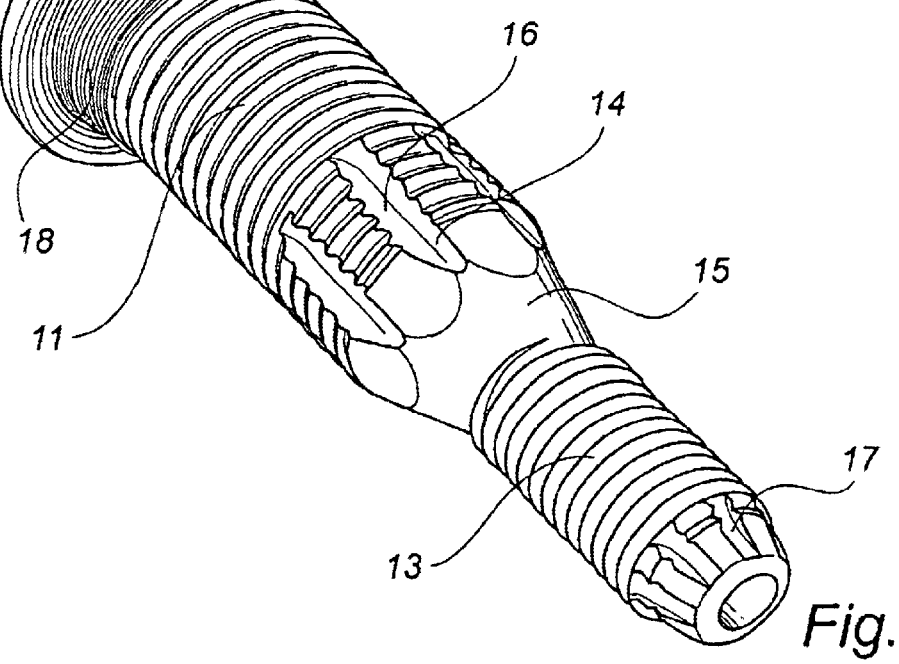
FIG. 2 is an opposite perspective view of the femur fixture shown in FIG. 1.

As can be seen in FIGS. 1–3, the intraosseous anchoring section 3 has proximal and distal cylindrical sections 11, 13 of different outer diameter, with the diameter of the proximal cylindrical section 11 being greater than that of the distal cylindrical section 13. The intraosseous anchoring section 3 further has a tapered terminal distal section 12, contiguous with the distal cylindrical section 13, a frusto-conical connecting section 15 connecting the proximal cylindrical section 11 to the distal cylindrical section 13, and a frusto-conical proximal section 18 connecting the proximal cylindrical section 11 to the head section 5.

The proximal cylindrical section 11 presents a screw-threaded outer surface for screwing into an outer bone cavity section 32 of said cavity. The distal cylindrical section 13 also presents a screw-threaded outer surface, for screwing into a narrow drilled hole 31, which is coaxial with said outer cavity section 32. The screw-threads of the proximal cylindrical section 11 have the same pitch and height as those of the distal cylindrical section 13.

Figure 7:
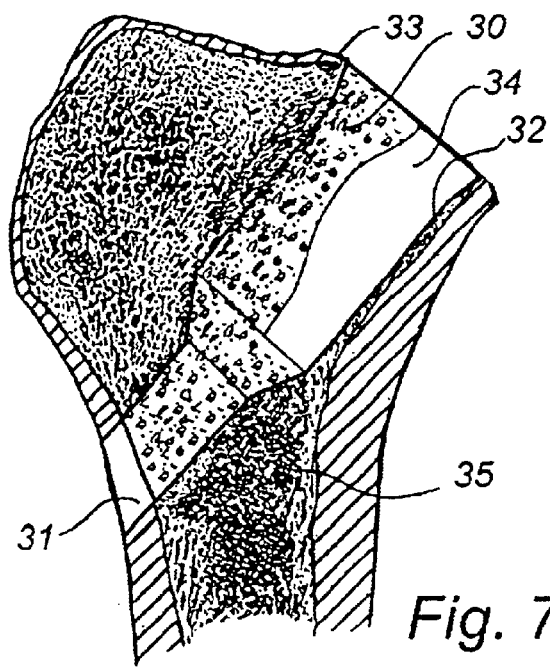
FIG. 7 is a fragmentary sectional view of the collum of the human femur, with a cavity formed therein for reception of the femur fixture.

The major diameters of the screw threads on the proximal and distal cylindrical sections 11, 13 are sized to be greater than the inner diameter of complementary cylindrical sections of the outer cavity section 32 and the drilled hole 31 provided in the cavity 30 of the femur neck (See FIG. 7). Accordingly, the intraosseous anchoring section 3 is able to be anchored in the cavity 30 by screwing of the femur fixture 1 into the cavity 30, with the screw threads on the proximal and distal cylindrical sections 11, 13 threading into the bone tissue in the boundary wall of the cavity 30.

Figure 8:
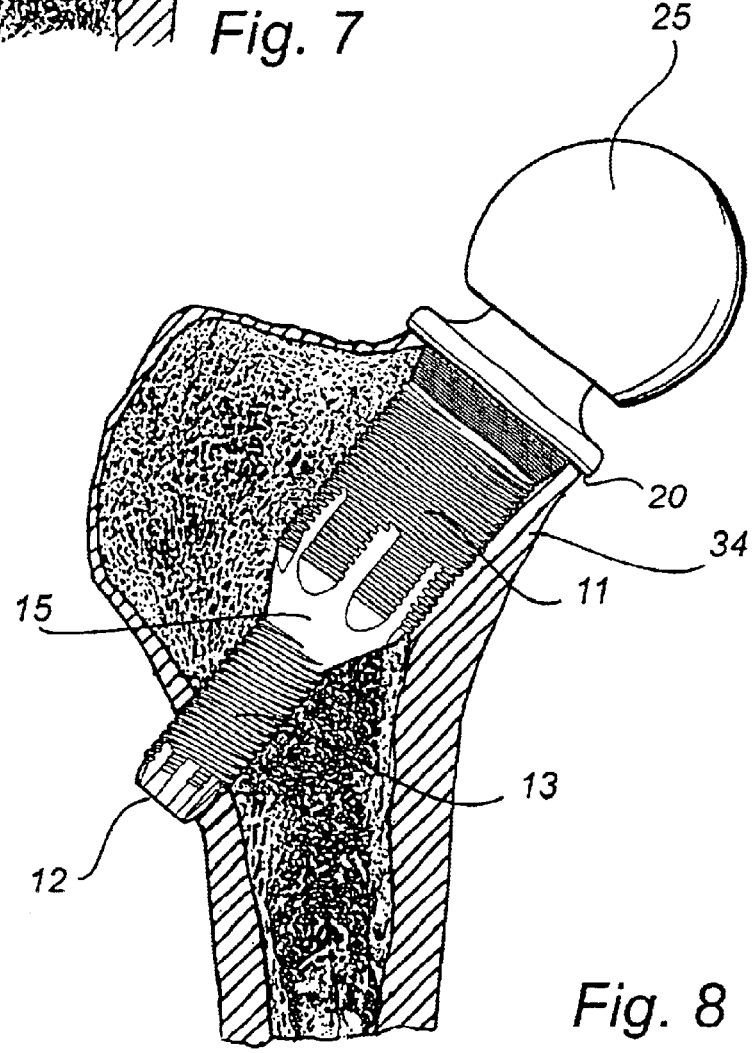
FIG. 8 is a fragmentary sectional view of the collum of the human femur, with the femur fixture inserted therein.

As seen in FIG. 8, the diameter of the proximal cylindrical section 11 is in fact sized such that the threads thereon register in the peripheral layer of cortical bone 34 in the femur neck, as outlined in WO93/16663 and WO97/25939. The threads on the proximal cylindrical section 11 are thus secured in the stronger cortical bone 34 as opposed to the spongier cancellous bone 35, thereby giving the femur fixture 1 greater fixation in the femur neck. Due to the fact that the femur dimensions can vary from patient to patient, the diameter of the proximal cylindrical section can vary in the range from approximately 16–26 mm (cf. FIGS. 3 and 8).

As illustrated in FIG. 8, the axial length of the intraosseous anchoring section 3 is such that in the anchored position of the intraosseous anchoring section 3, the distal end 12 thereof projects through the lateral cortex 34 of the femur.

Figure 5:
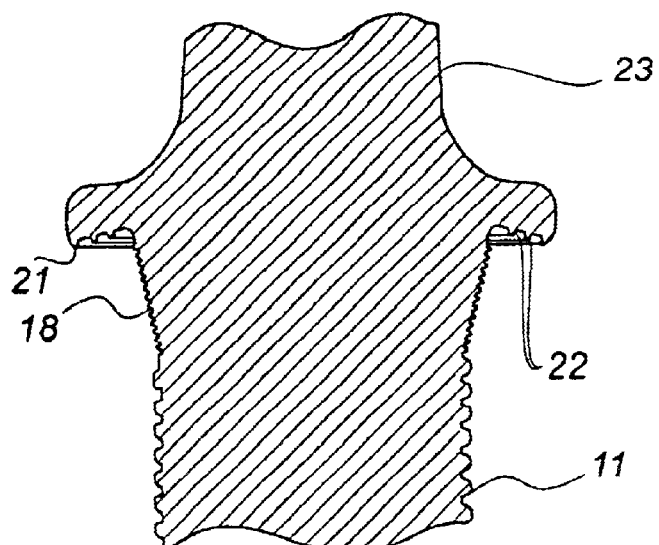
FIG. 5 is an enlarged fragmentary sectional view showing the tapered proximal section and the head of the femur fixture.

With reference to FIGS. 3–5, the frusto-conical proximal section 18 also has threads thereon. The height of these threads is 0.2 mm (so-called microthreads) which is less than that of the threads on the proximal and distal cylindrical sections 11, 13. Further, the frusto-conical proximal section 18 is sized so that the microthreads engage with the cortex 34 of the femur neck at the resected surface. In the embodiment described herein, the frusto-conical terminal proximal section 18 has a flank angle of approximately 12°, and an axial extent of approximately 8 mm.

The distal diameter of the proximal section 18 is adapted to the diameter of the neighbouring proximal cylindrical section 11, such that there are no sharp edges in the transition area between the frusto-conical proximal section 18 and the proximal cylindrical section 11. Consequently, the proximal diameter of the frusto-conical proximal section 18 is in the range of approximately 20–30 mm.

The diameter of the distal cylindrical section 13 does not have to be varied in dependence of the femur dimensions of the patient. The diameter of the distal cylindrical section 13 is approximately 11 mm, or within the range of 10–12 mm.

The frusto-conical connecting section 15 interconnects the proximal and distal cylindrical sections 11, 13 to one another. In this embodiment, the diameters at the respective end of the connecting section 15 correspond to the diameters of the proximal and distal cylindrical sections 11, 13, respectively. In other words, the distal end of the connecting section 15 has essentially the same diameter as the distal cylindrical section 13, and the proximal end of the connecting section 15 has essentially the same diameter as the proximal cylindrical section 11.

As a result of the fact that the diameter of the proximal cylindrical section 11 can be varied between different femur fixtures, while the diameter of the distal cylindrical section 13 is not varied, the dimensions of the connecting section will be varied in accordance with the varying difference in diameter between the proximal cylindrical section 11 and the distal cylindrical section 13. Since the axial extent of the connecting section is kept relatively short, i.e. within the range of approximately 7.5–10.5 mm, the flank angle of the connecting section can vary from approximately 200 for the narrowest fixture alternative, up to approximately 370 for the widest fixture alternative.

In the herein described embodiment of the invention, the surface of the frusto-conical connecting section 15 is provided with a grit-blasted surface for promoting the osseointegration between the surface and the surrounding cancellous bone tissue. The surface could also, or alternatively, be provided with a screw thread profile for promoting said osseointegration and improve the anchorage of the femur fixture 1. As a further alternative, the frusto-conical connecting section 15 may be left smooth, even polished.

As can be seen in FIGS. 2 and 3, bridging the boundary between the proximal cylindrical section 11 and the frusto-conical connecting section 15 are a series of equi-spaced, circumferentially-arranged, sharp-edged cutting recesses or notches 14 for self-tapping into a precut outer bone cavity section 32. The cutting recesses 14 each communicate with a channel 16 in the proximal cylindrical section 11 for autologous transplantation of the bone cut by the cutting recesses 14 as the femur fixture 1 is screwed into the bore in the femur neck, as detailed in WO97/25939.

Further, bridging the boundary between the distal cylindrical section 13 and the tapered terminal distal section 12 are also a series of short, sharp-edged circumferentially-arranged cutting recesses 17 for the distal cylindrical section 13 to be self-tapped into said drilled, relatively narrow hole 31.

Figure 6:
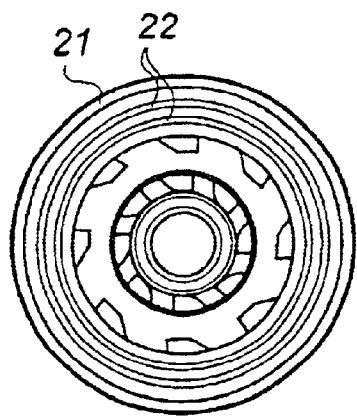
FIG. 6 is a bottom view of the femur fixture.

With reference to FIGS. 1, 7 and 8, the head section of the femur fixture 1 has a collar section 20 and a tapered mounting section 23 for the ball component 25 of the hip-joint prosthesis to be mounted on. The mounting section 23 is provided with a recess 24 for reception of the ball component 25. The collar section 20 delimits the insertion of the intraosseous anchoring section 3 into the bore in the femur neck by abutting with the resected femur section 33 adjacent the opening to the cavity 30. As can be seen in FIG. 5, the distal surface 21 (FIG. 5) is inclined inwardly for mating with a correspondingly inclined bone surface the resected femur section 33 (FIG. 7). The angle of inclination in the embodiment herein described is approximately 15°. Further, as seen in FIG. 6, for improved anchorage and osseointegration, the distal surface 21 of the collar section 20 is provided with radially spaced, circumferential beads 22, said beads having a height of approximately 0.3 mm.

The surgical procedures described in WO93/16663 and WO97/25939 for implanting the femur fixtures disclosed therein can also be adapted for implantation of the femur fixture 1 and as such are incorporated herein by reference.

The anchorage of the femur fixture 1 is primarily reliant on the registration of the threads in the bone of the femur, principally the registration of the threads on the proximal cylindrical section 11 in the cortex 34 of the femur neck and the registration of the threads on the distal cylindrical section 13 in the lateral cortex 34 of the femur. This is in distinction to femur fixtures which rely on a thrust plate mechanism for their fixation, for example as in GB-A-2033755.

The femur fixture 1 herein described with reference to the accompanying figures can be varied in numerous ways within the scope of the invention. For instance, the femur fixture 1 could be in the form of an assembly in which the component parts are assembled (i) for insertion thereof laterally into the bore as a one-piece structure, as disclosed in WO93/16663, or (ii) by connecting the parts together in the bore, as disclosed in WO93/01769. The femur fixture 1 could also be made from any biocompatible patible material of strength sufficient to withstand the loads imposed upon it in situ.

Figure 9:
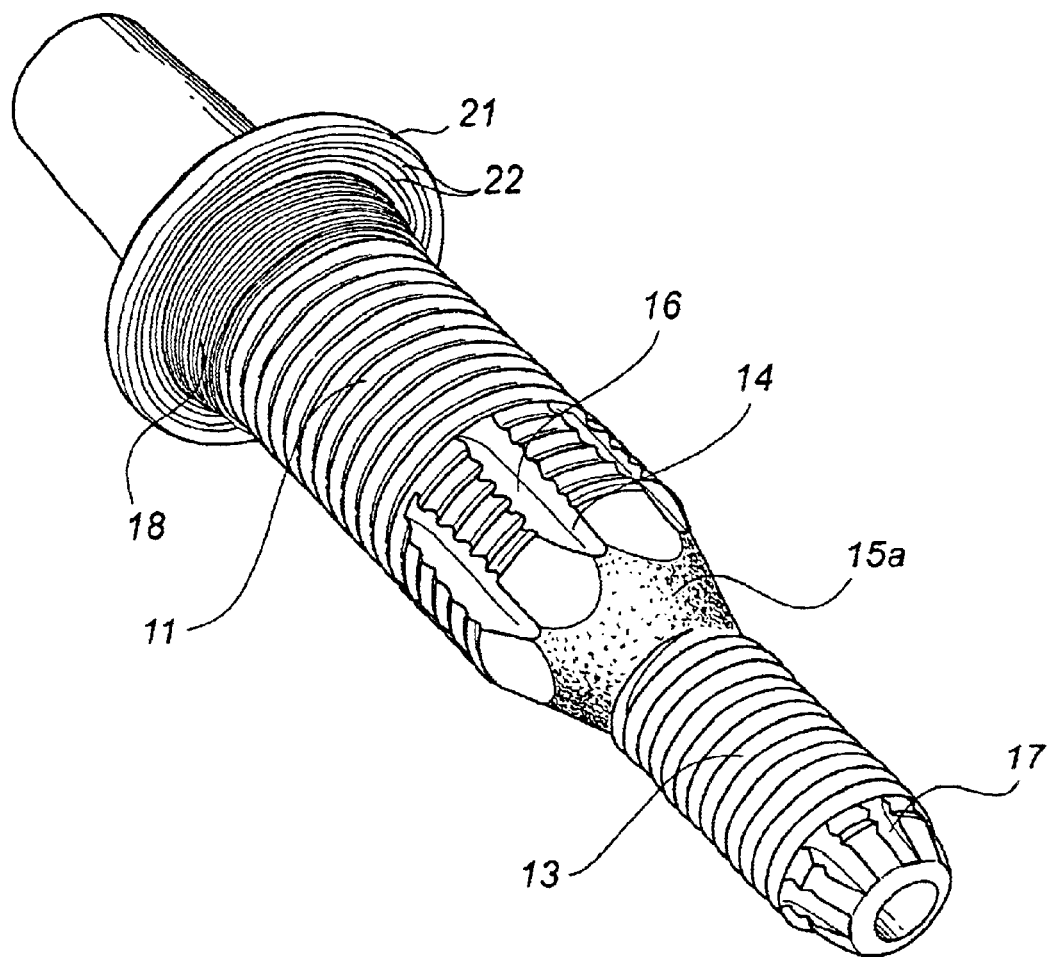
FIG. 9 is a perspective view similar to FIG. 2 of the femur fixture with a roughened surface which is at least partially blasted.
Figure 10:
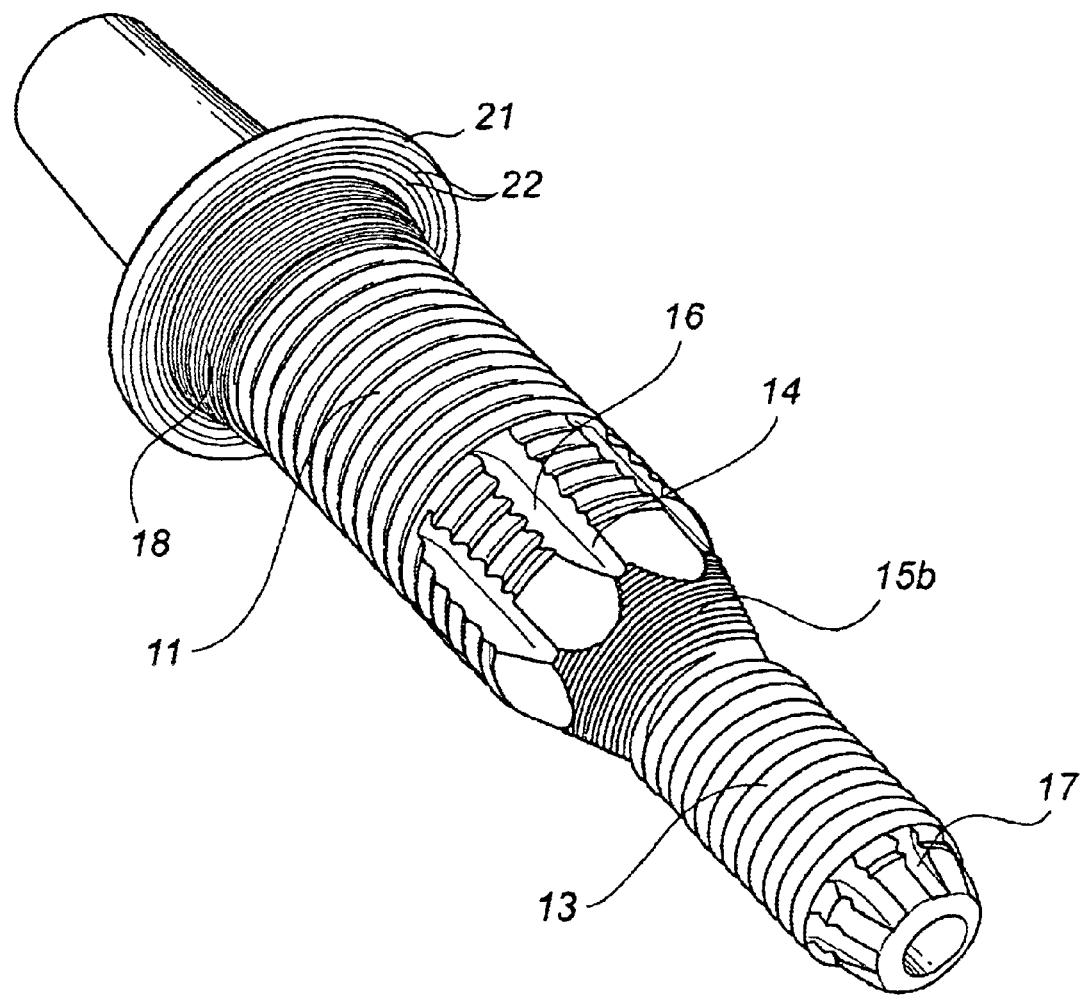
FIG. 10 is a perspective view similar to FIG. 9 of the femur fixture with a connecting section having circumferential beads.

Turning now to FIG. 9 and embodiment of the femur fixture is shown with a connecting section 15a having a roughened surface which is at least partly a blasted surface. In FIG. 10, a connecting section 15b is shown having a roughened surface 15 which is at least partly provided with a circumferentially oriented roughness in the form of circumferential beads that have a height less than that of the screw thread profiles of the first and second cylindrical sections and no greater than 0.3 mm.

Figure 11:
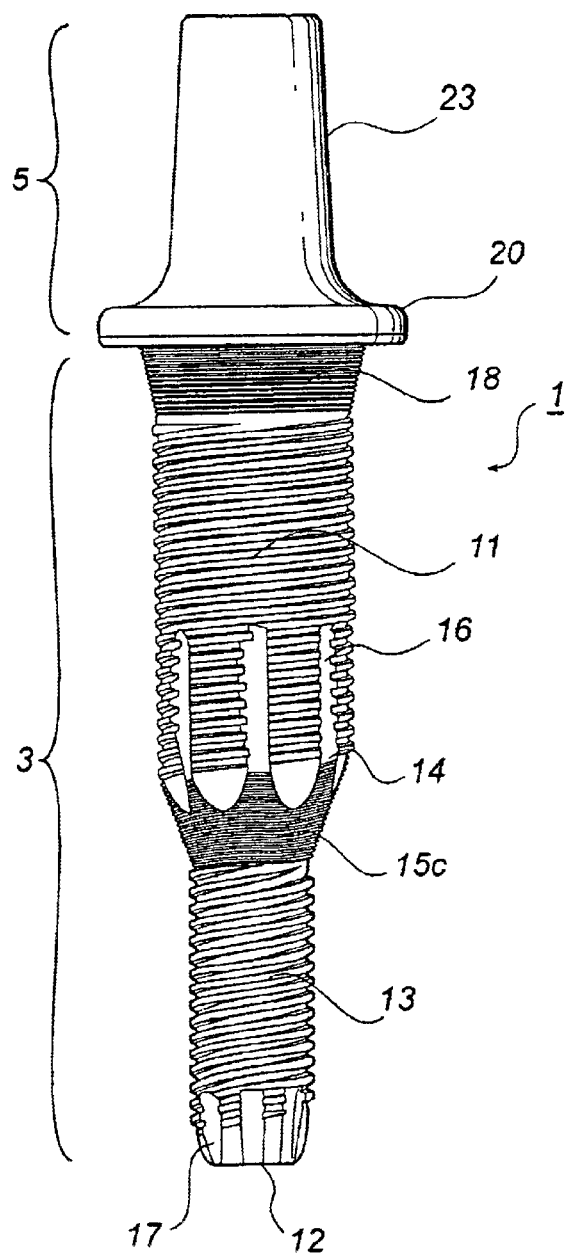
FIG. 11 is a longitudinal side view similar to FIG. 3 of the femur fixture with a connecting section having a screw thread profile.
Figure 12:
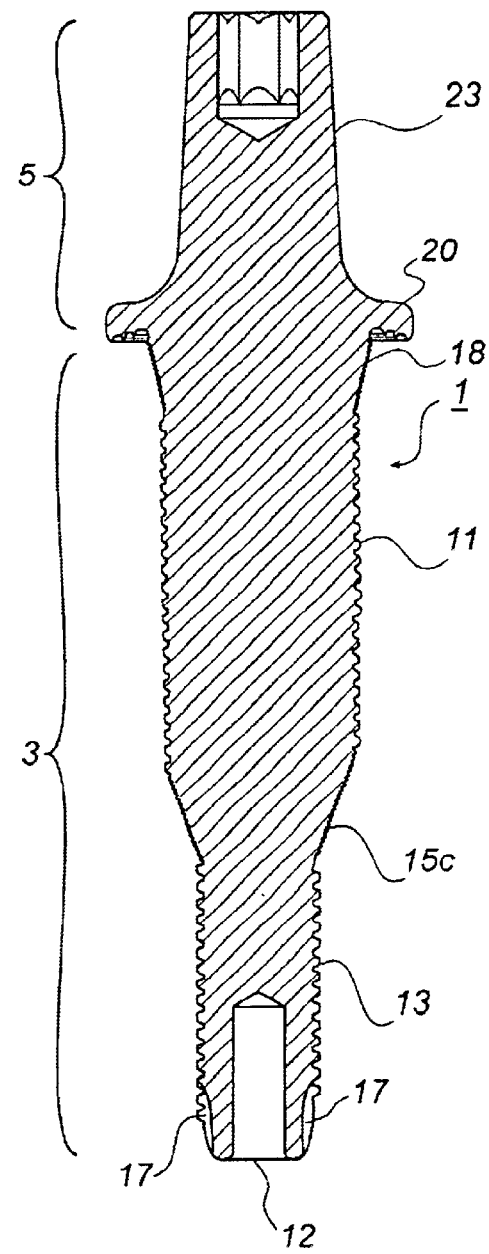
FIG. 12 is a longitudinal sectional view similar to FIG. 4 of the femur fixture with a connecting section having the screw profile.
Figure 13:
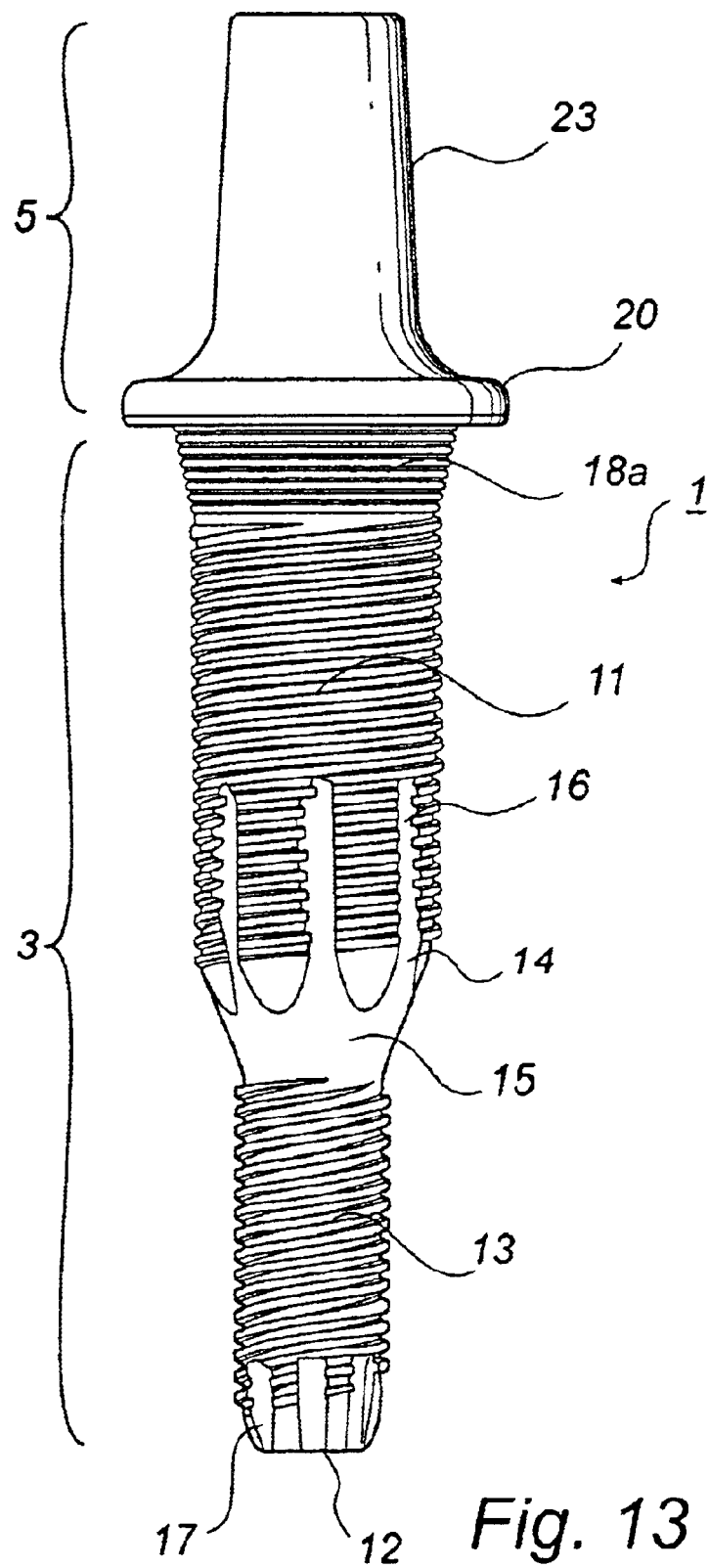
FIG. 13 is a longitudinal side view similar to FIG. 11 of the femur fixture with a connecting section have circumferential beads.
Figure 14:
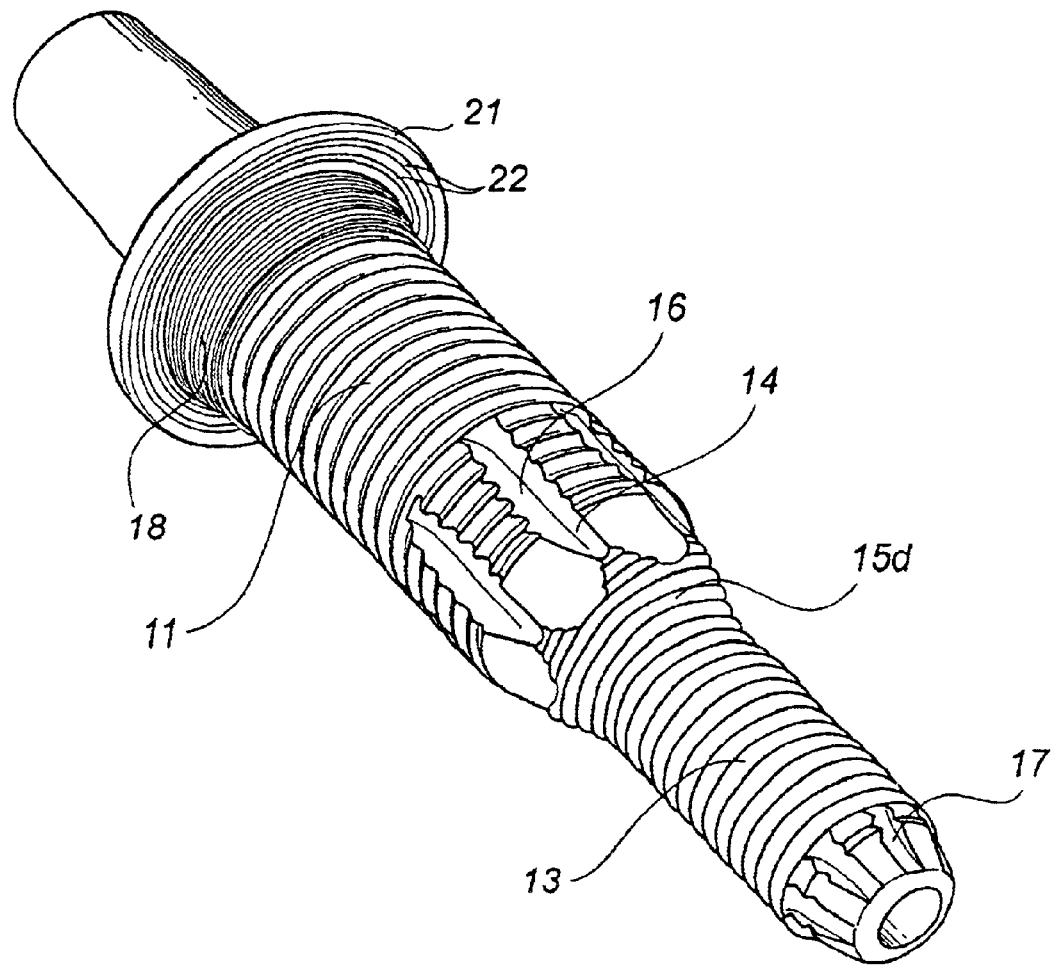
FIG. 14 is a perspective view similar to FIG. 10 of the femur fixture with a connecting section having a screw thread.

In FIGS. 11 and 12, a connecting section 15c is shown having a roughened surface which is at least partly provided with a circumferentially orientated roughness in the shape of a screw thread profile that has a height less than that of the screw thread profiles of the first and second cylindrical sections and no greater than 0.3 mm. FIG. 13 illustrates a proximal section which is provided with a roughness 18a in the form of circumferential beads. In FIG. 14, a connecting section 15d is illustrated having a roughened surface which is at least partly provided with a circumferentially oriented roughness in the shape of a screw thread profile that has a height essentially the same as that of the screw thread profiles of the first and second cylindrical sections.

It will be appreciated that the invention has been described with reference to an exemplary embodiment and that the invention can be varied in many different ways within the scope of the appended claims. For instance, the implant is not confined to use as a femur fixture for a hip-joint prosthesis. As an example, the implant could take the form of a bone fixation screw. It will further be appreciated that the use in the appended claims of reference numerals from the Figures of drawings is for the purposes of illustration and not to be construed as having a limiting effect on the claims.

What is claimed is:

1. An orthopaedic fixture for an orthopaedic prosthesis, said fixture being arranged to be screwed into a bore having an open end in a resected bone surface and arranged to be permanently anchored in bone tissue, comprising a ball carrying portion and an intraosseous anchoring structure of a generally circular cross-section, said anchoring structure comprising a first cylindrical section of a first diameter and a second cylindrical section of a second diameter, said second diameter being less than said first diameter, said first and second cylindrical sections each being provided with a screw thread profile of the same hand, characterized in that said anchoring structure comprises a tapered connecting section provided between and interconnecting said first and second cylindrical sections, wherein the diameters at the respective end of the connecting section correspond to the diameters of the first and the second cylindrical sections, respectively, and in that said fixture comprises a collar section which is arranged proximally to said first cylindrical section of the anchoring structure adapted to abut said resected bone surface.

2. A fixture as claimed in claim 1, wherein the implant is a femur fixture of a hip-joint prosthesis.

3. A fixture as claimed in claim 1, wherein said connecting section has a frusto-conical shape.

4. A fixture as claimed in claim 3, wherein said connecting section at one end has a base diameter essentially equal to said first diameter of said first cylindrical section, and at the other end has a top diameter essentially equal to said second diameter of said second cylindrical section.

5. A fixture as claimed in claim 3, wherein said connecting section has a flank angle in the range of 10°–50°.

6. A fixture as claimed in claim 1, wherein said connecting section is at least partly provided with a roughened surface.

7. A fixture as claimed in claim 6, wherein said roughened surface is at least partly a blasted surface.

8. A fixture as claimed in claim 6, wherein said roughened surface is at least partly provided with a circumferentially oriented roughness.

9. A fixture as claimed in claim 8, wherein said circumferentially oriented roughness is in the form of circumferential beads.

10. A fixture as claimed in claim 9 wherein said circumferential beads has a height less than that of the screw thread profiles of said first and second cylindrical sections.

11. A fixture as claimed in claim 10, wherein the height of said circumferential beads is no greater than 0.3 mm.

12. A fixture as claimed in claim 8, wherein said circumferentially oriented roughness is in the shape of a screw thread profile.

13. A fixture as claimed in claim 12, wherein the screw thread profile of said connecting section differs from the screw thread profiles of said first and second cylindrical sections.

14. A fixture as claimed in claim 13, wherein the screw thread profile of said connecting section has a height less than that of the screw thread profile of said first and second cylindrical sections.

15. A fixture as claimed in claim 14, wherein the screw thread profile of said connecting section is in the form of microthreads.

16. A fixture as claimed in claim 15, wherein the height of said microthreads is no greater than 0.3 mm.

17. A fixture as claimed in claim 12, wherein the heights of the screw thread profiles of said first and second cylindrical sections and said connecting section are essentially the same.

18. A fixture as claimed in claim 1, wherein said connecting section is at least partly provided with a smooth surface.

19. A fixture as claimed in claim 1, wherein the entire surface of said connecting section is smooth.

20. A fixture as claimed in claim 1, wherein one or more self-tapping cutting recesses are provided at least in part on said connecting section.

21. A fixture as claimed in claim 1, wherein said implant comprises a head section, and wherein said anchoring structure comprises a tapered proximal section being provided between and interconnecting said first cylindrical section and said head section.

22. A fixture as claimed in claim 21, wherein said proximal section has a frustro-conical shape.

23. A fixture as claimed in claim 22, wherein said proximal section at the end interfacing said first cylindrical section has a diameter essentially equal to said first diameter of said first cylindrical section.

24. A fixture as claimed in claim 22, wherein said proximal section has a flank angle in the range of 8°–15°.

25. A fixture as claimed in claim 21, wherein said proximal section is at least partly provided with a circumferentially oriented roughness.

26. A fixture as claimed in claim 25, wherein said circumferentially oriented roughness is in the form of circumferential beads.

27. A fixture as claimed in claim 25, wherein said circumferentially oriented roughness is in the form of a screw thread profile.

28. A fixture as claimed in claim 26, wherein the height of said circumferentially oriented roughness is no greater than 0.3 mm.

29. A fixture as claimed in claim 21, wherein said collar section forms part of the head section.

30. A fixture as claimed in claim 29, wherein said distal surface is inclined inwardly towards the body of the collar section.

31. A fixture as claimed in claim 30, wherein said distal surface is inclined inwardly at an inclination angle within the range of 10°–20°.

32. A fixture as claimed in claim 29, wherein said distal surface is concave.

33. A fixture as claimed in claim 29, wherein said distal surface is provided with radially spaced circular beads.

34. A fixture as claimed in claim 33, wherein said circular beads have a height in the range of 0.1–0.5 mm.

\* \* \* \* \*